(12) United States Patent
Addison et al.

(10) Patent No.: US 8,660,625 B2
(45) Date of Patent: Feb. 25, 2014

(54) SIGNAL PROCESSING SYSTEMS AND METHODS FOR ANALYZING MULTIPARAMETER SPACES TO DETERMINE PHYSIOLOGICAL STATES

(75) Inventors: Paul Stanley Addison, Edinburgh (GB); James Nicholas Watson, Dunfermline (GB); Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1547 days.

(21) Appl. No.: 12/242,915

(22) Filed: Oct. 1, 2008

(65) Prior Publication Data
US 2010/0016680 A1 Jan. 21, 2010

Related U.S. Application Data

(60) Provisional application No. 61/080,957, filed on Jul. 15, 2008.

(51) Int. Cl.
*A61B 5/026* (2006.01)
*A61B 5/0452* (2006.01)

(52) U.S. Cl.
USPC .......................................... 600/323; 600/301

(58) Field of Classification Search
USPC ................... 436/900; 73/23.3; 600/301, 323; 382/128
See application file for complete search history.

(56) References Cited

U.S. PATENT DOCUMENTS

| | | |
|---|---|---|
| 4,289,141 A | 9/1981 | Cormier |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,967,995 A | 10/1999 | Shusterman et al. |

(Continued)

FOREIGN PATENT DOCUMENTS

| JP | 09-084776 | | 3/1997 | |
|---|---|---|---|---|
| WO | WO 01/25802 | * | 4/2001 | ............. G01R 23/00 |

(Continued)

OTHER PUBLICATIONS

Claims of U.S. Appl. No. 13/076,281, commonly assigned.*

(Continued)

*Primary Examiner* — Kamal Saeed
*Assistant Examiner* — Janet L Coppins

(57) ABSTRACT

The present disclosure relates to signal processing systems and methods, and more particularly, to systems and methods for analyzing multiparameter spaces to determine changes in a physiological state. In embodiments, a first signal and a second signal may be obtained, from which a first plurality of values of a physiological parameter may be determined. At least one of the signals also may be used to generate a scalogram derived at least in part from the signal. A second plurality of values may be determined based at least in part on a feature in the scalogram. The first and second plurality of values may then be associated, and a physiological state may be analyzed using the associated first and second values. In an embodiment, the signals may be PPG signals and the associated first and second values may include a parameter scatter plot that may permit a user to determine changes in a patient's ventilation state over time.

11 Claims, 11 Drawing Sheets

(56) References Cited

U.S. PATENT DOCUMENTS

| | | |
|---|---|---|
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,931,269 B2 | 8/2005 | Terry |
| 7,001,337 B2 | 2/2006 | Dekker |
| 7,020,507 B2 | 3/2006 | Scharf |
| 7,035,679 B2 * | 4/2006 | Addison et al. ............... 600/323 |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2005/0043616 A1 | 2/2005 | Chinchoy |
| 2005/0065417 A1 | 3/2005 | Ali et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/62152 | 8/2001 |
| WO | WO 03/055395 | 7/2003 |
| WO | 2004075746 A | 9/2004 |
| WO | WO 2004/105601 | 12/2004 |
| WO | WO 2005/096170 | 10/2005 |
| WO | WO 2006/085120 | 8/2006 |

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm For The Determination Of Respiratory Rate From The Photoplethysmogram," Journal of Clinical Monitoring and Computing, 2006.

Leonard, Paul., Clifton, David, Addison, Paul S., Watson, James N., Beattie, Tom "An Automated Algorithm For Determining Respiratory Rate By Photoplethysmogram In Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

Poudov V S: "The comparison of possibilities of continuous and discrete wavelet transforms for MCG data processing" Electron Devices and Materials, 2004. Proceedings, 5th Annual 2004 International Siberian Workshop on Erlagol, Altai Jul. 1-5, 2004, Piscataway, NJ, USA, IEEE Jul. 1, 2004, pp. 138-142, XP010741839, ISBN: 978-5-7782-0463-8, the whole document.

* cited by examiner

SIGNAL PROCESSING SYSTEMS AND METHODS FOR ANALYZING MULTIPARAMETER SPACES TO DETERMINE PHYSIOLOGICAL STATES

CROSS-REFERENCE TO RELATED APPLICATION

This application claims the benefit of U.S. Provisional Application Ser. No. 61/080,957, entitled "Signal Processing Systems and Methods for Analyzing Multiparameter Spaces to Determine Physiological State," filed Jul. 15, 2008, which is hereby incorporated by reference herein in its entirety.

SUMMARY

The present disclosure generally relates to signal processing systems and methods, and more particularly, to systems and methods for analyzing multiparameter spaces to determine changes in a physiological state. Multiple parameters may be derived at least in part from the same signal or signals and also may be compared. In an embodiment, a signal or a number of signals may be processed and analyzed to obtain clinically relevant information For example, the signal may include two photoplethysmograph (PPG) signals that may be analyzed to derive blood oxygen saturation information about a patient from whom the PPG signals were obtained. The blood oxygen saturation information may be used in conjunction with the processed PPG signals to also evaluate changes in the patient's ventilation over time.

In an embodiment, the signal or signals may be processed in any suitable manner to obtain the clinically relevant information (e.g., the blood oxygen saturation information). For example, the signals may be analyzed using the "ratio of ratios" method, in which a ratio is taken between changes in one signal and changes in the other signal after both signals have passed through human tissue. Alternatively, a wavelet transform may be performed on one or more signals to generate one or more scalograms that may be further analyzed to obtain the clinically relevant information. In an embodiment, slope values may be plotted on a histogram to derive the clinically relevant information. The clinically relevant information may be analyzed in conjunction with the processed signal or signals to obtain further useful information using any suitable method. For example, the blood oxygen saturation information may be plotted against respiration information. The respiration rate or scale values may be obtained using any suitable method. For example, the respiration rate or scale values may be obtained from the ridge of the respiration component of any suitable scalogram.

In an embodiment, comparing blood oxygen saturation information with respiration information may be useful in determining physiologically relevant information. For purposes of clarity, and not by way of limitation, the primary embodiment disclosed herein is a process for determining physiological states from wavelet-transformed signals, such as PPG signals. For example, respiratory depression and hypoxemia may be analyzed from wavelet-transformed PPG signals. In an embodiment, the shape or the slope of the plot (e.g., a parameter scatter plot obtained by plotting blood oxygen saturation against respiration information), or how the plot compares with a threshold region, may provide information regarding the patient's ventilation. In an embodiment, a plot of data points, such as a parameter scatter plot, may be analyzed to determine whether the plot or the parameter scatter plot is located within one or more threshold regions. The threshold region may be empirically derived at least in part from physiological data obtained from any suitable number of individuals, and the threshold region also may be initially calibrated using physiological data obtained from a particular individual. This may enable a user or a system to evaluate a particular patient's physiological state. For example, a parameter scatter plot oriented within one threshold region, whether that threshold region is universally applicable to many individuals or has been calibrated to apply to a particular patient, may indicate that the patient is properly ventilated. By contrast, a parameter scatter plot oriented within another threshold region may indicate that the patient is experiencing a respiratory depression or hypoxemia.

In an embodiment, the shape, or the distribution, of the plotted data points may be used instead of or in addition to threshold regions to determine clinically relevant information. For example, a slope (e.g., a dominant slope) of the data distribution may be used to provide further information about the patient's physiological state. If the slope derived at least in part from the data distribution has a value above a certain threshold, for example, that may be an indication of a proper physiological state. If the derived slope has a value that falls below the threshold) that may be an indication of a poor physiological state.

In an embodiment, a method for analyzing a physiological state is provided. The method may include obtaining a first signal and a second signal, determining a first plurality of values of a physiological parameter using at least the first signal and the second signal, deriving a scalogram from the first signal, determining a second plurality of values based at least in part on a feature in the scalogram, associating the first plurality of values with the second plurality of values, and analyzing the physiological state based at least in part on the associated first and second plurality of values.

In an embodiment, a system for analyzing a physiological state is provided. The system may include an input signal generator for generating a first signal and a second signal, a processor coupled to the input signal generator, and an output coupled to the input signal generator. The output may be capable of displaying information based at least in part on the analysis of the physiological state. The processor may be capable of determining a first plurality of values of a physiological parameter based at least in part upon at least the first signal and the second signal, deriving a scalogram from the first signal, determining a second plurality of values based at least in part on a feature in the scalogram, associating the first plurality of values with the second plurality of values, and analyzing the physiological state based at least in part on the associated first and second plurality of values.

In an embodiment, a computer-readable medium for use in analyzing a physiological state is provided. The computer-readable medium may include computer program instructions recorded thereon for obtaining a first signal and a second signal, determining a first plurality of values of a physiological parameter using at least the first signal and the second signal, deriving a scalogram from the first signal, determining a second plurality of values based at least in part on a feature in the scalogram, associating the first plurality of values with the second plurality of values, and analyzing the physiological state based at least in part on the associated first and second plurality of values.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
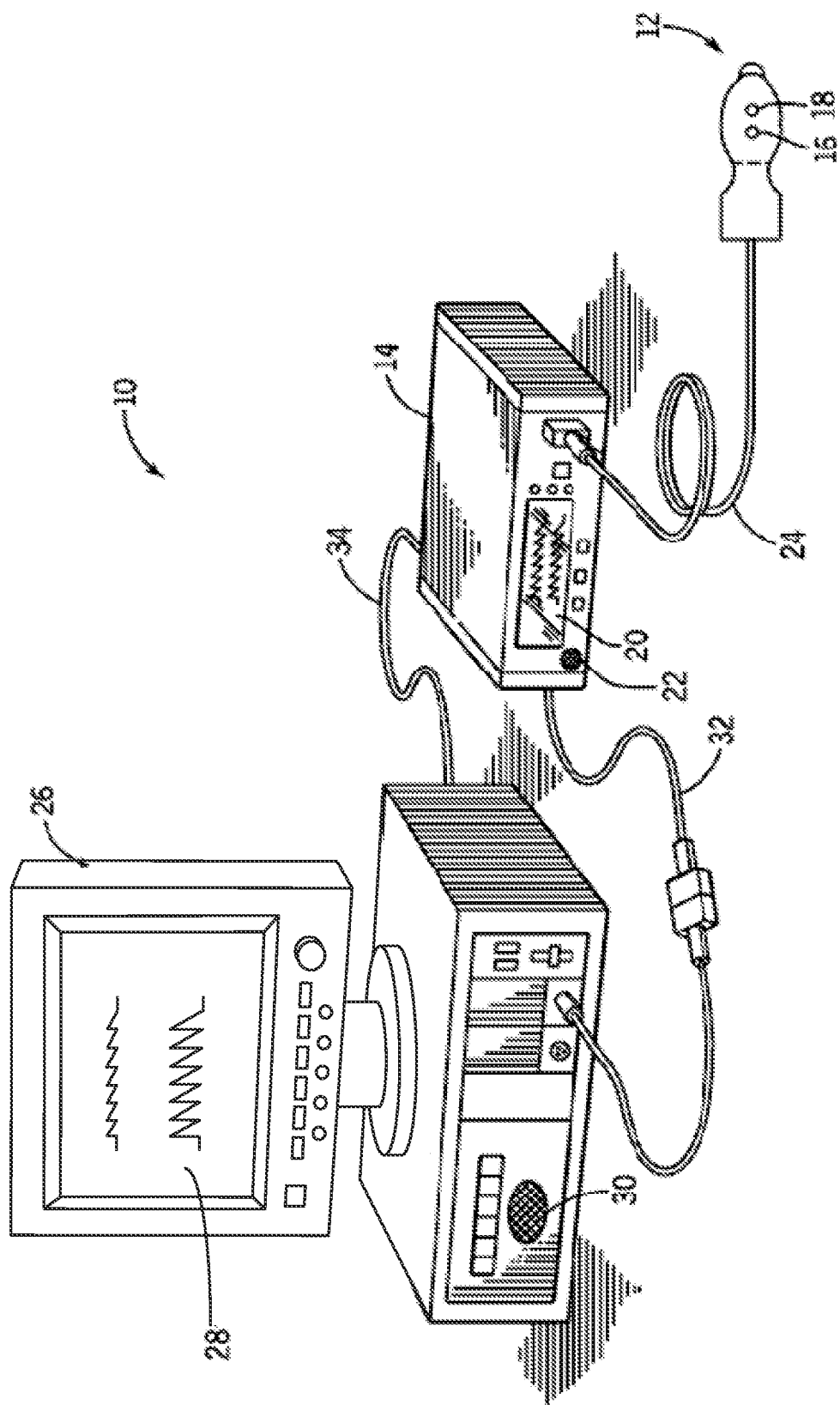
FIG. 1 shows an illustrative pulse oximetry system in accordance with an embodiment.

The present disclosure relates to signal processing and, more particularly, the present disclosure relates to systems and methods for analyzing multiparameter spaces to determine changes in physiological state, such as, for example, changes in a patient's respiration.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I}. \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to an embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO₂" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
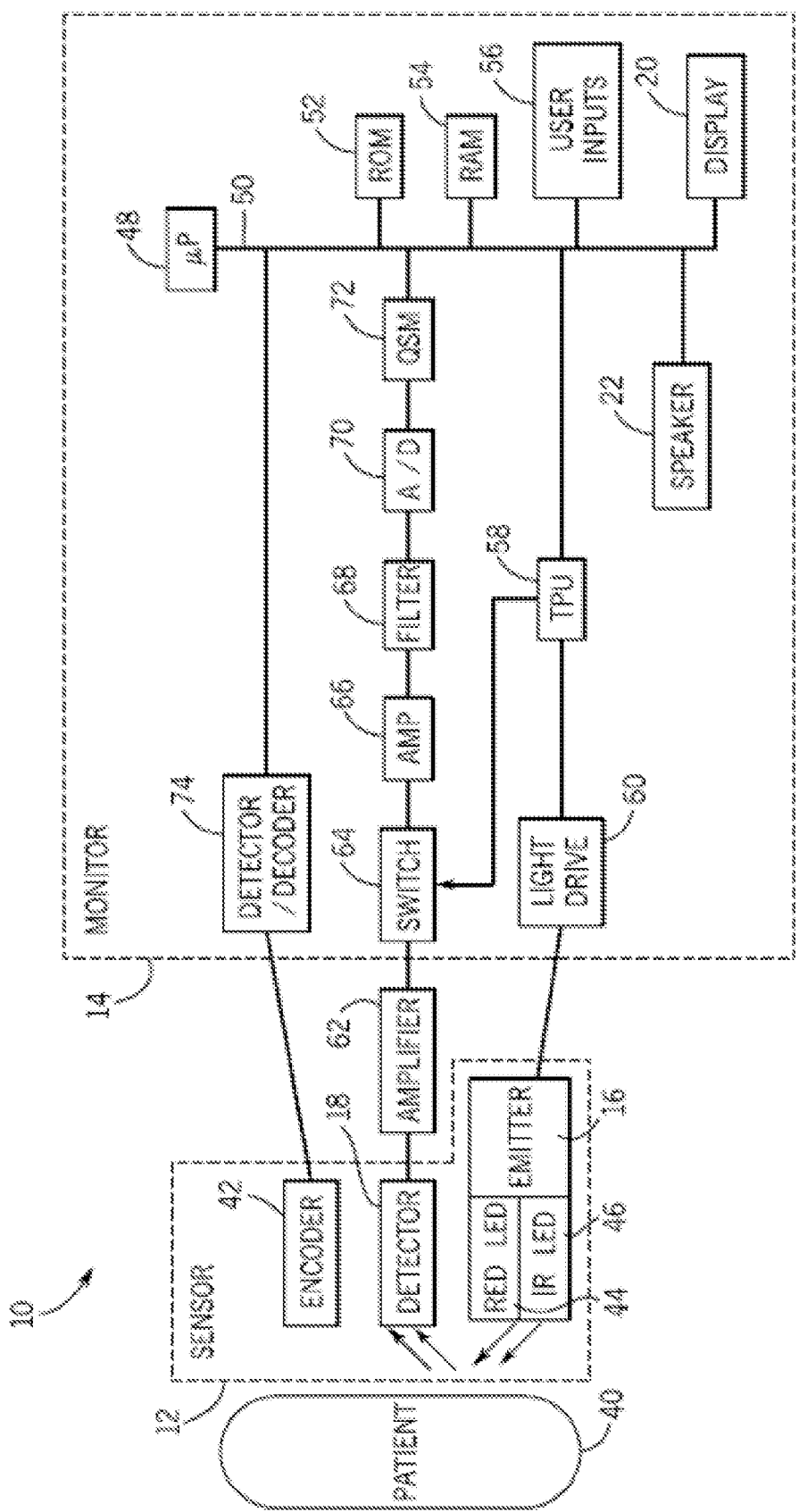
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations preformed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \qquad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \qquad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \qquad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
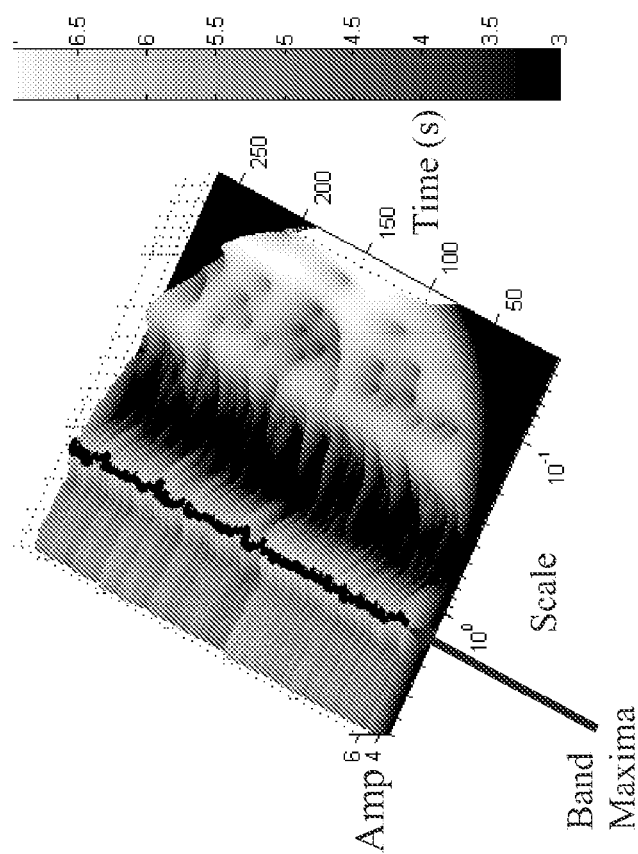
FIGS. 3(a) and 3(b) show illustrative views of a scalogram derived from a PPG signal in accordance with an embodiment.
Figure 3A:
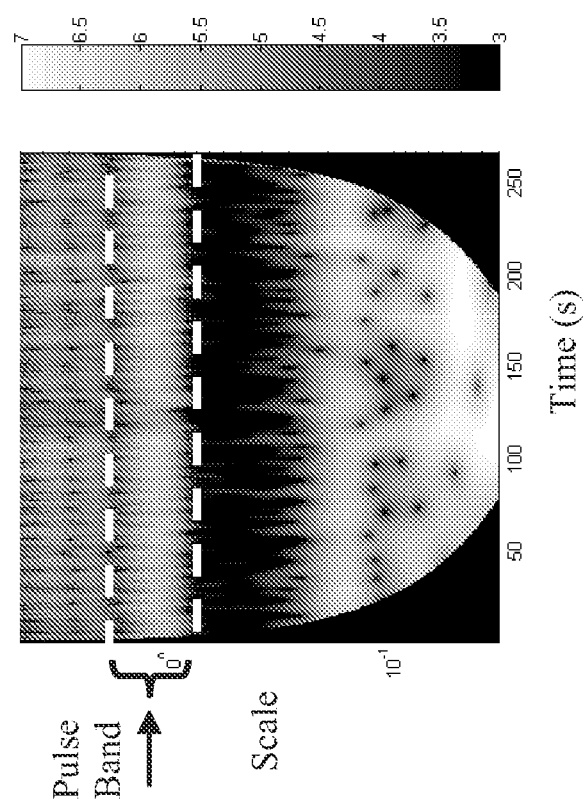

In embodiments, pertinent repeating features in a signal may give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

In embodiments, by mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
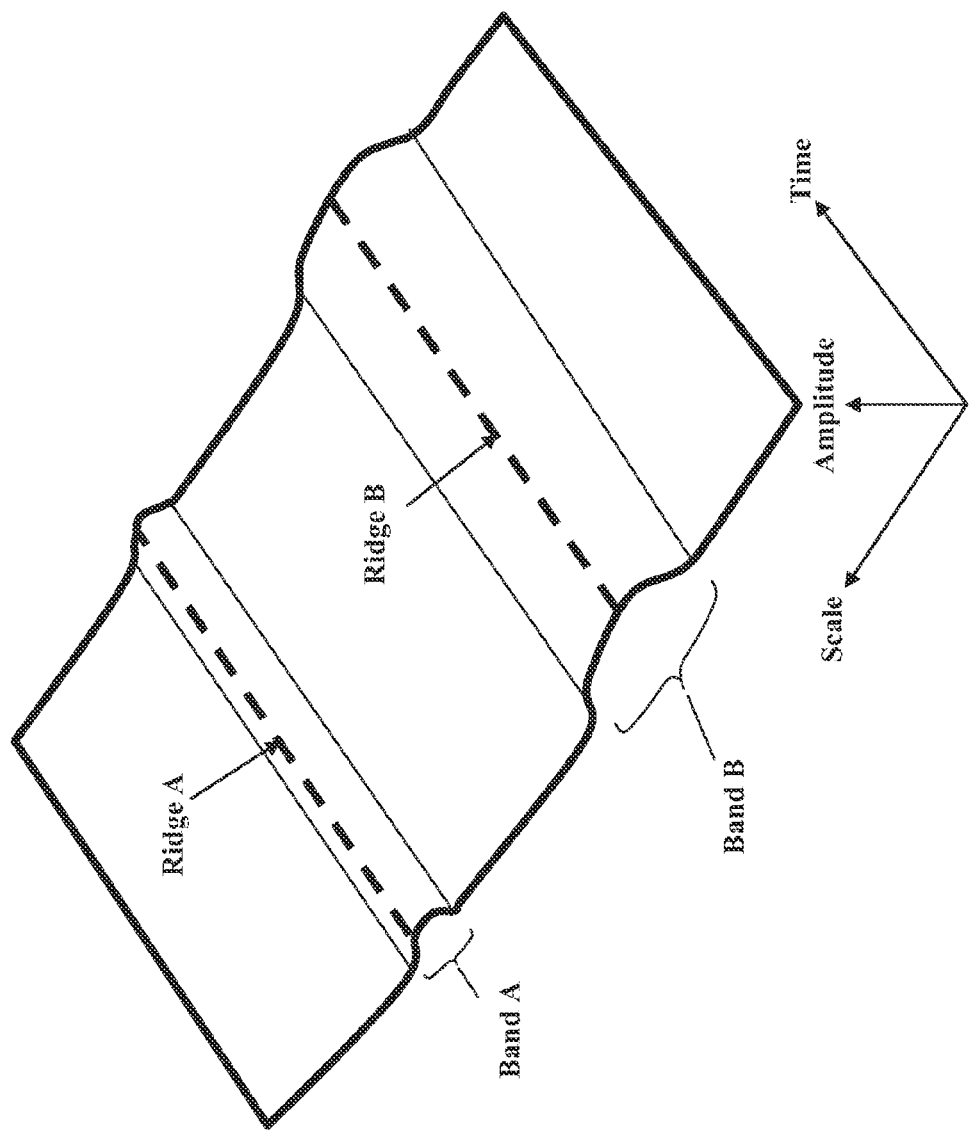
FIG. 3(c) shows an illustrative scalogram derived from a signal containing two pertinent components in accordance with an embodiment.
Figure 3D:
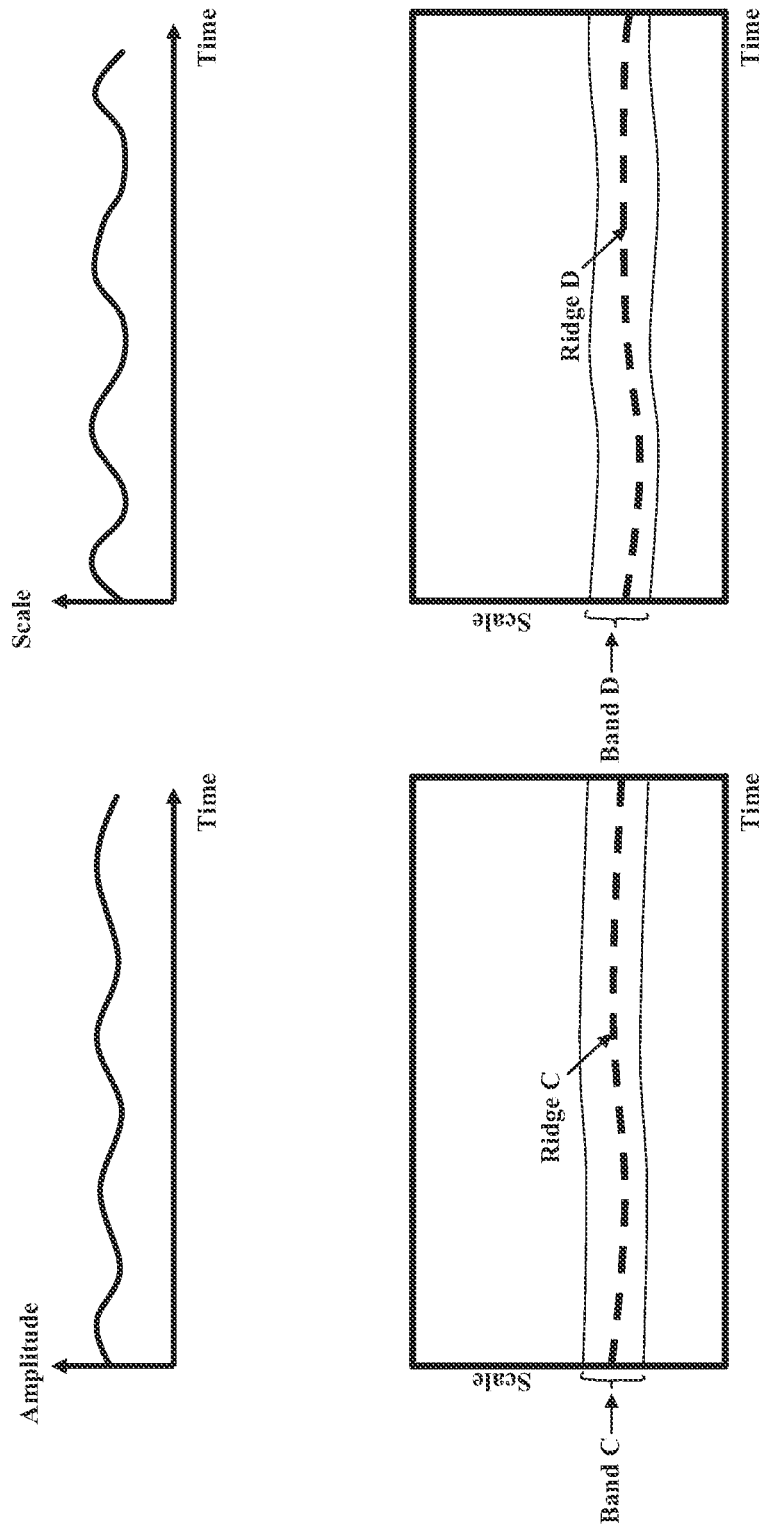
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some embodiments, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{dadb}{a^2} \quad (15)$$

which may also be written as:

$$x(t) = \frac{1}{C_g} \int_{-\infty}^{\infty} \int_0^{\infty} T(a, b) \psi_{a,b}(t) \frac{dadb}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
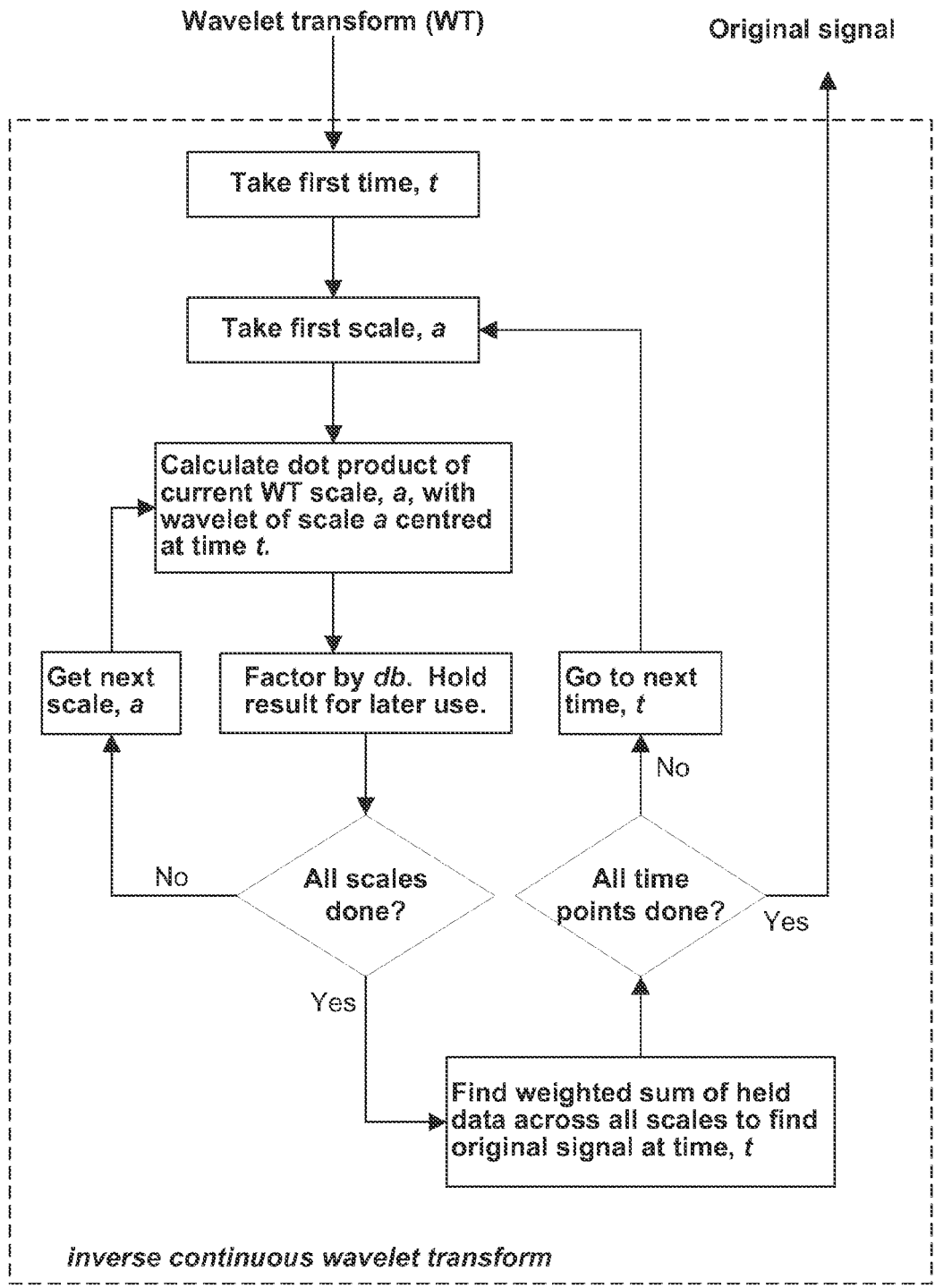
FIGS. 3(e) and 3(f) are flow charts of illustrative steps involved in performing an inverse continuous wavelet transform in accordance with embodiments.
Figure 3F:
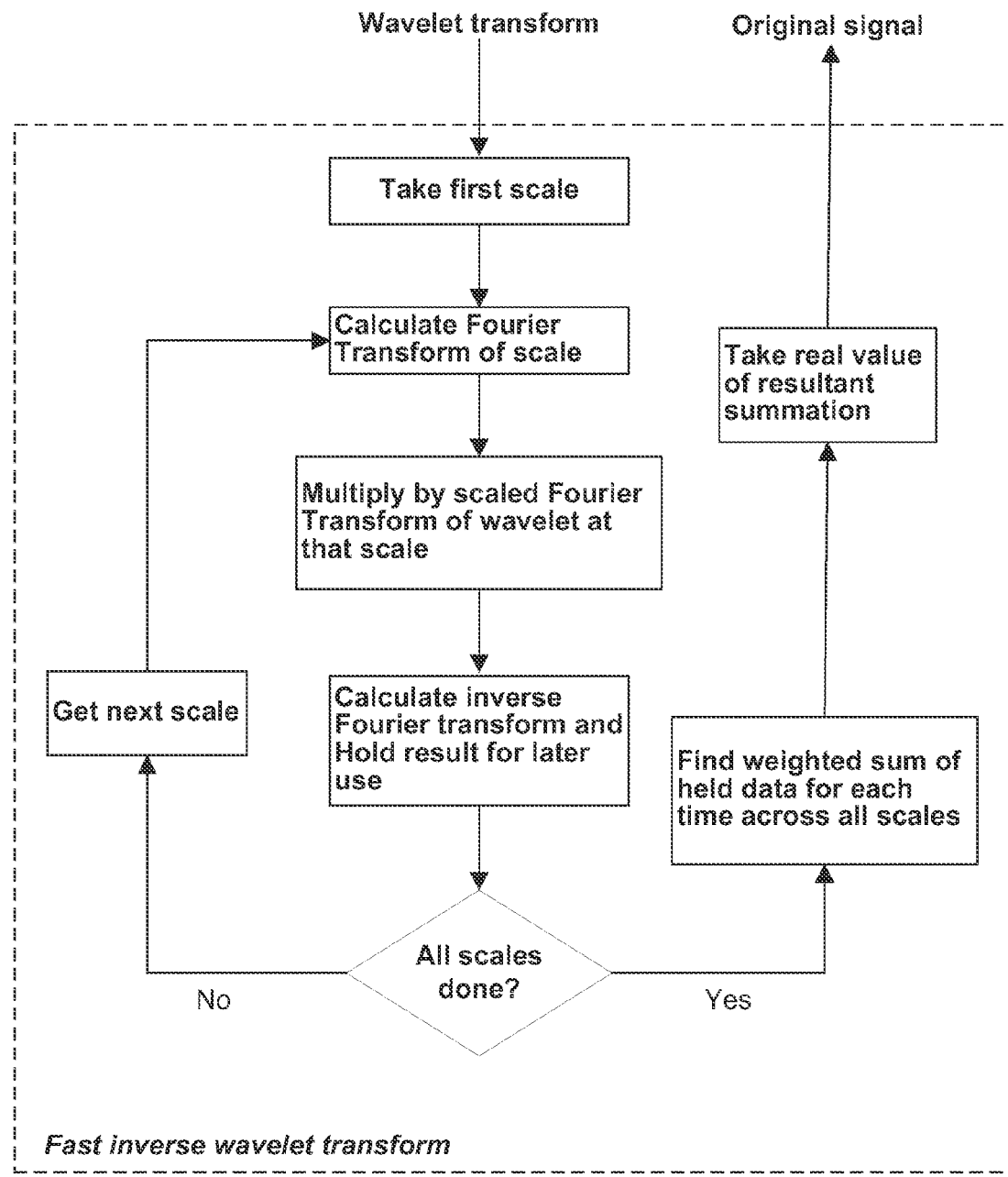

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
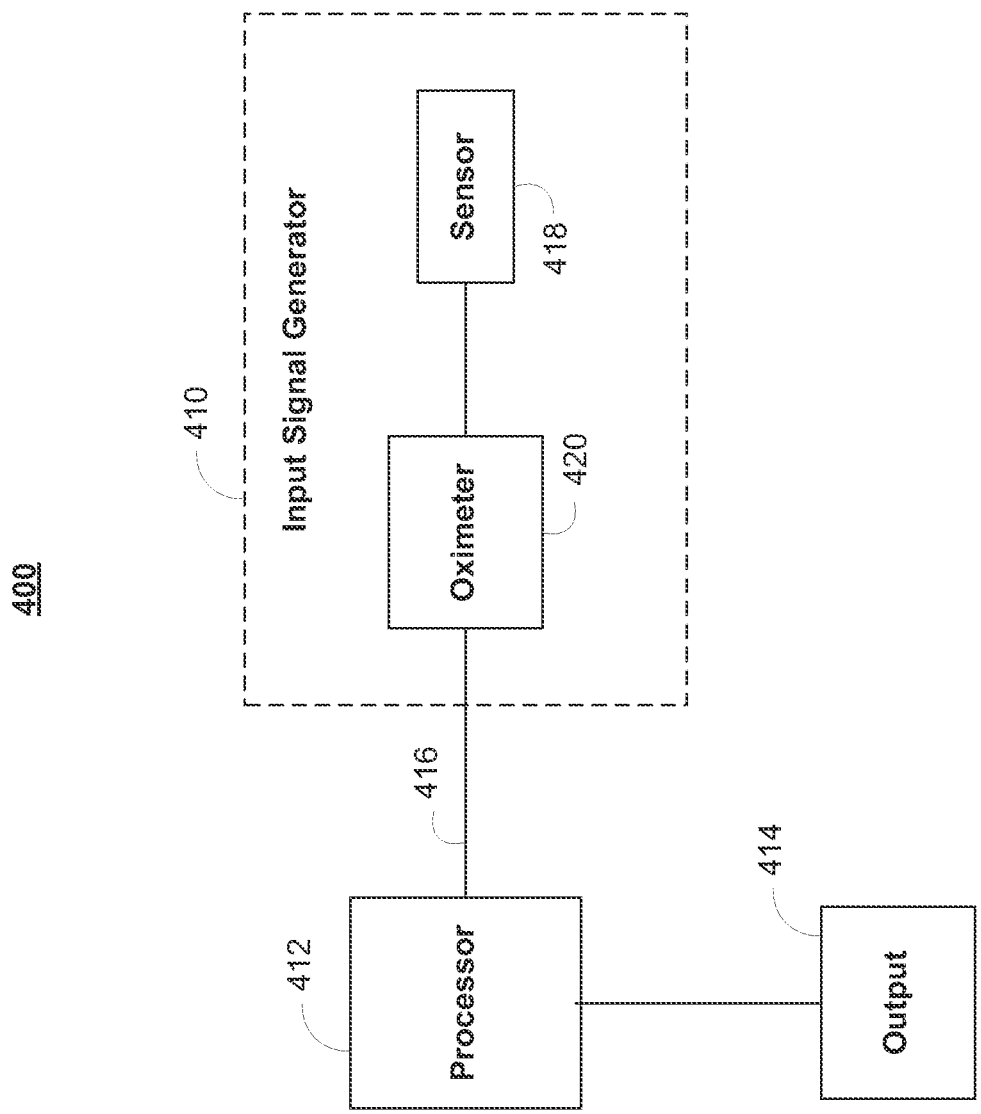
FIG. 4 is a block diagram of an illustrative continuous wavelet processing system in accordance with some embodiments.

FIG. 4 is an illustrative continuous wavelet processing system 400 in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

In some embodiments, processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14, according to an embodiment.

The multiparameter space analysis of the present disclosure will now be discussed in reference to FIGS. 5-7.

In an embodiment, a signal or a number of signals may be processed to obtain clinically relevant information. The signal may include any suitable signal, including a continuous signal, a discrete signal, a signal formed from multiple data points, or features of a scalogram or a Lissajous figure. For example, the signal may include two PPG signals that may be analyzed to derive blood oxygen saturation information about a patient 40 from whom the PPG signals were obtained (e.g. using sensor 12 (FIG. 2) or sensor 418 of input signal generator 410 (FIG. 4)). The blood oxygen saturation information may be derived by microprocessor 48 (FIG. 2) or processor 412 (FIG. 4) operating in real time on PPG signal samples from QSM 72 (FIG. 2) or from samples stored in RAM 54 (FIG. 2). The clinically relevant information may also be used to derive further useful information. For example, the blood oxygen saturation information derived from the processed PPG signals may be used in conjunction with respiration information processed from one of the PPG signals to also evaluate changes in the patient's ventilation over time.

The signal or signals may be processed in any suitable manner to obtain the clinically relevant information. For example, the signals may be analyzed using the "ratio of ratios" method, in which a ratio is taken between changes in one signal and changes in the other signal after both signals have passed through human tissue. The underlying mathematical detail is discussed above and may also be found in the general literature. The resulting ratio of ratios may be used to derive the clinically relevant information, such as blood oxygen saturation. Alternatively, a wavelet transform may be performed on one or more signals to generate one or more scalograms, as described above with respect to FIGS. 3(a) and 3(b) that may be further analyzed to obtain the clinically relevant information. For example, a three-dimensional Lissajous figure and a subsequently selected two-dimensional Lissajous figure may each be derived from the scalograms. The slope of the two-dimensional Lissajous figure may be used to derive the desired information, as described in U.S. Patent Pub. No. 2006/0258921, published Nov. 16, 2006, entitled "Method of Analyzing and Processing Signals," which is incorporated by reference herein in its entirety. U.S. Patent Pub. No. 2006/0258921 also describes other techniques for deriving desired information from wavelet transforms of signals (e.g., PPG signals) that may be used in connection with this disclosure. Processor 412 or microprocessor 48 may include any suitable software, firmware, and/or hardware, and/or combinations thereof for performing the calculations associated with the continuous wavelet transforms of the present disclosure as well as the calculations associated with any suitable interrogations of the scalograms, including the calculation of slope values and the creation of one or more histograms.

The slope of the two-dimensional Lissajous figure, from which the clinically relevant information may be derived, may be determined using any suitable approach. In an embodiment, slope values may be determined between each data point of the Lissajous figure and the slope values may be plotted on a histogram to derive the clinically relevant information. Such a method is described more fully in Watson et al., U.S. application Ser. No. 12/242,882, entitled "Signal Processing Systems and Methods for Determining Slopes of Electronic Signals," filed Sep. 30, 2008, which is incorporated by reference herein in its entirety. In another embodiment, slope values may be determined between any suitable origin point selected from the plot containing the Lissajous figure and each data point of the Lissajous figure, and the slope values may be plotted on a histogram to derive the clinically relevant information. Such a method is described more fully in Watson et al., U.S. application Ser. No. 12/242, 881, entitled "Signal Processing Systems and Methods for Determining Slope Using an Origin Point," filed Sep. 30, 2008, which is incorporated by reference herein in its entirety. In some embodiments, the histogram may be smoothed prior to analysis using, for example, a smoothing technique such as Gaussian kernel smoothing, low pass filtering, or any other suitable means.

The clinically relevant information may be analyzed in conjunction with the processed signal or signals to obtain further useful information using any suitable method. In an embodiment, the blood oxygen saturation information obtained using any of the methods described above or using any other suitable method may be plotted by processor 412 or microprocessor 48 against respiration information obtained from either of the scalograms derived from the PPG signals.

The respiration information may correspond to band B of the selected scalogram (e.g. only one scalogram from one PPG signal may be selected), and band B may be obtained as described above with respect to FIG. 3(c). Changes in the scale value in the ridge of band B may indicate changes in the respiration rate of patient 40. For example, in a healthy patient 40, a change in respiration rate may correspond to a change in blood oxygen saturation. A change in respiration rate that does not correspond to a change in blood oxygen saturation, however, may indicate that patient 40 has a ventilation problem. The ridge of band B may be followed in wavelet space for a given period of time, and the scale values of the ridge may be plotted.

In some embodiments, the ridge of band A (FIG. 3(c)) may be followed in wavelet space and the RAP and RSP signals may be extracted as described above with respect to FIG. 3(d). Using SWFD, as described above, a further wavelet decomposition may be performed on the RAP and RSP signals to allow for information (e.g., respiration information) in the region of band B to be made available as band C and band D (FIG. 3(d)).

For each plotted respiration scale value, the blood oxygen saturation amplitude corresponding to the scale value, as derived by processor 412 or microprocessor 48, may also be plotted by processor 412 or microprocessor 48. In an embodiment, the plot may be a parameter scatter plot. The resulting plot or figure may be evaluated to determine physiologically relevant information about patient 40. For example, the shape or the slope of the plot or the figure (e.g., a parameter scatter plot) may provide information regarding the ventilation of patient 40. In an embodiment the respiration rate may be computed by processor 412 or microprocessor 48 based at least in part on the ridge of the respiration band from the selected scalogram and the respiration rate may be plotted in place of the scale values of the ridge.

Figure 5:
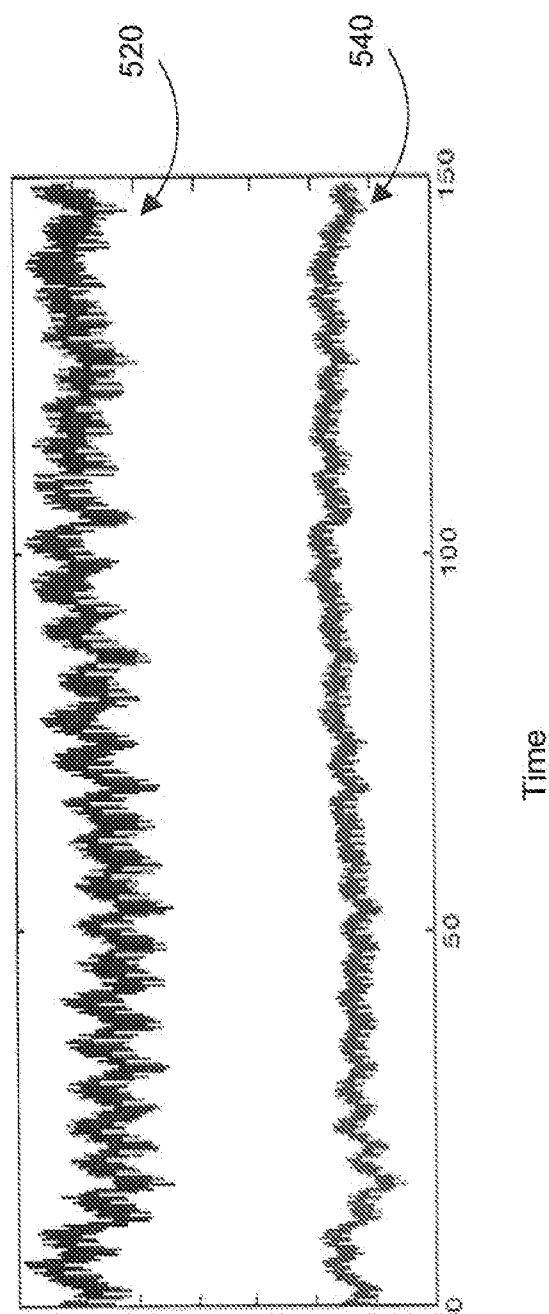
FIG. 5 shows a plot of two signals detected in accordance with an embodiment.

FIG. 5 shows a plot of two signals detected in accordance with an embodiment in which PPG signals are employed. In this embodiment, one PPG signal may include a red light signal 520 and another PPG signal may include an infrared light signal 540 obtained from a pulse oximeter sensor, as described above. Red light signal 520 and infrared signal 540 may be plotted as shown in FIG. 5 after passing through a portion of the blood perfused tissue of patient 40 (e.g., a fingertip, a toe, a foot). The pulse oximeter sensor may transmit red light signal 520 and infrared light signal 540 to any suitable processing unit (e.g., processor 412 or microprocessor 48) for further analysis. For example, analyzing the ratio between changes in the red light signal 520 and changes in the infrared light signal 540 after both signals have passed through human tissue may be useful in determining the blood oxygen saturation of patient 40.

Figure 6:
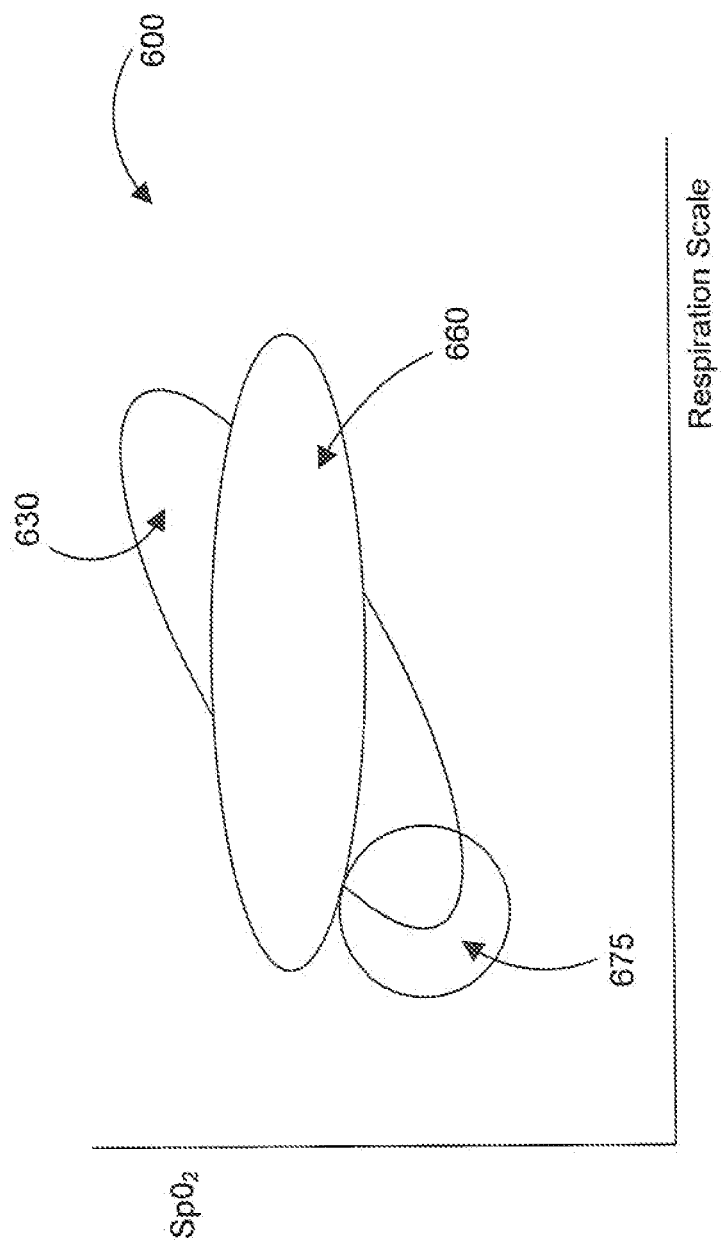
FIG. 6 shows threshold regions in a multiparameter plot in accordance with an embodiment.

FIG. 6 shows a multiparameter plot that may include threshold regions derived in accordance with an embodiment. Plot 600 may include axes related to any suitable unit of measure, such as axes related to time, amplitude, scale, length, frequency, distance, or any other suitable unit of measure. In FIG. 6, plot 600 may include a blood oxygen saturation ("SpO$_2$") axis and a respiration scale value axis. Plot 600 may be used to plot changes in SpO$_2$ values, as derived by processor 412 or microprocessor 48, as a function of changes in respiration scale values, also as derived by processor 412 or microprocessor 48, over a defined time period (not shown). The SpO$_2$ values and respiration scale values may be obtained using any suitable method, such as any of the methods described above.

Plot 600 is shown as including threshold regions 630 and 660. Threshold regions 630 and 660 may be derived or determined using any suitable method. Threshold region 630, for example, may be a region where a plot of respiration scale values versus SpO$_2$ values may be expected for a healthy patient 40. On the other hand, threshold region 660 may be a region where a plot of respiration scale values versus SpO$_2$ values are expected for a patient 40 who has a health problem such as a ventilation problem. Threshold regions 630 and 660 may be empirically derived at least in part from physiological data obtained from any suitable number of individuals. In an embodiment, threshold regions 630 and/or 660 also may be initially calibrated using physiological data obtained from a particular individual. Threshold regions 630 and 660 are discussed in further detail below.

The respiration scale values may be obtained using any suitable method. For example, the respiration scale values may be obtained by processor 412 or microprocessor 48 from the ridge of the respiration component of any suitable scalogram, as described above with respect to FIGS. 3(a), 3(b), and 3(c). The scalogram may include any suitable number of ridges at any suitable scale value. In an embodiment, red light signal 520 and infrared light signal 540 may each include components relating to the pulse of a patient, the breathing rate of a patient, and one or more signal artifacts (e.g., noise). The signal components related to pulse rate and breathing rate may contain higher energy than other signal components. Scalograms derived at least in part from the application of a wavelet transform to each of red light signal 520 and infrared light signal 540, respectively, may include a ridge at a particular scale value that may be related to the pulse component and another ridge at a particular scale value that may be related to the breathing component of red light signal 520 and infrared light signal 540. The respiration information may correspond to band B of the selected scalogram, as described above with respect to FIG. 3(c), and the ridge of the respiration component of interest may correspond to ridge B. Whereas signals 520 and 540 may both be used to calculate changes in blood oxygen saturation amplitude, the respiration scale values may be obtained from the ridge of the respiration component of a scalogram derived at least in part from either signal 520 or 540 (e.g., using the ridge of the respiration component of the scalogram derived at least in part from infrared light signal 540 or red light signal 520). The respiration scale values may also be obtained by performing a secondary wavelet decomposition of RAP and/or RSP signals associated with the pulse ridge from a scalogram derived at least in part from either signal 520 or 540. The respiration scale values may also be obtained using any other suitable technique.

The orientation of threshold regions 630 and 660 on plot 600 may be based at least in part on clinically relevant information. Therefore, analyzing a plot of data points on plot 600 to determine whether the plot is located within threshold region 630 or within threshold region 660 may enable system 10, system 400, or a user of system 10 or system 400 to evaluate the physiological state of patient 40. For example, threshold region 630 may be oriented such that when the respiration scale value increases, the SpO$_2$ value also increases at a particular rate. This orientation may be consistent with an expected increase in a healthy individual's blood oxygen saturation level as the respiration rate (e.g., number of breaths in a defined time period) or respiration scale increases. Threshold region 630 may be assembled from empirical data obtained from any suitable number of patients. In an embodiment, threshold region 630 also may be calibrated, or reoriented, with respect to a particular patient based upon empirical data obtained from the patient. For example, threshold region 630 may include one orientation and be located in one position on plot 600 for a young, healthy child, and threshold region 630 may include a different orientation and/or be located in a different position on plot 600 for an elderly patient that experiences respiratory difficulty.

In an embodiment, region 675 may indicate a central respiratory depression, in which the central nervous system of patient 40 may no longer be triggering or stimulating the breathing mechanism, thereby reducing the patient's breathing rate. The orientation of region 660 may indicate that as the respiration rate or scale value increases, the SpO$_2$ value may increase only slightly, or may not change. This orientation may be consistent with a ventilation problem, or a "ventilation-perfusion mismatch," in which the blood oxygen saturation level of patient 40 may not be altered by an increase or decrease in breathing rate. Such a mismatch may be an indication of hypoxemia, and thus plot 600 may be useful in evaluating the respiratory state of patient 40 as a result of obtaining signals 520 and 540 from a pulse oximeter sensor 12 coupled to patient 40. As with threshold region 630, threshold region 660 may be assembled from empirical data obtained from any suitable number of patients and also may be calibrated with respect to a particular patient.

In an embodiment, plot 600 may include a parameter scatter plot obtained from plotting blood oxygen saturation values against corresponding respiration scale values and the parameter scatter plot may lie within either region 630 or region 660. The parameter scatter plot may be derived by processor 412 or microprocessor 48 using any suitable method. A parameter scatter plot oriented within region 630 may indicate proper ventilation, as may be expected for a healthy patient from whom data may be obtained to derive the parameter scatter plot. By contrast, a parameter scatter plot oriented within region 660 may indicate that the patient does not have proper ventilation.

In an embodiment, the shape, or the distribution, of the data points plotted in plot 600 may be used instead of or in addition to threshold regions to determine clinically relevant information. For example, a slope (e.g., a dominant slope) of the data point distribution may be used to provide further information about the patient's ventilation. The slope of the data points can be determined by processor 412 or microprocessor 48 using any suitable method. In one suitable approach, a least squares line fitting method may be used. In another suitable approach, a dominant slope may be calculated from the data points using the methods described in U.S. application Ser. No. 12/242,882, and U.S. application Ser. No. 12/242,881. If the slope derived at least in part from the data distribution has a value above a certain threshold, for example, that may be an indication of proper ventilation of patient 40. If the derived slope has a value that falls below the threshold, that may be an indication of poor ventilation of patient 40. The derived slope may be analyzed using any suitable method to provide further information about the physiological state of patient 40.

Figure 7:
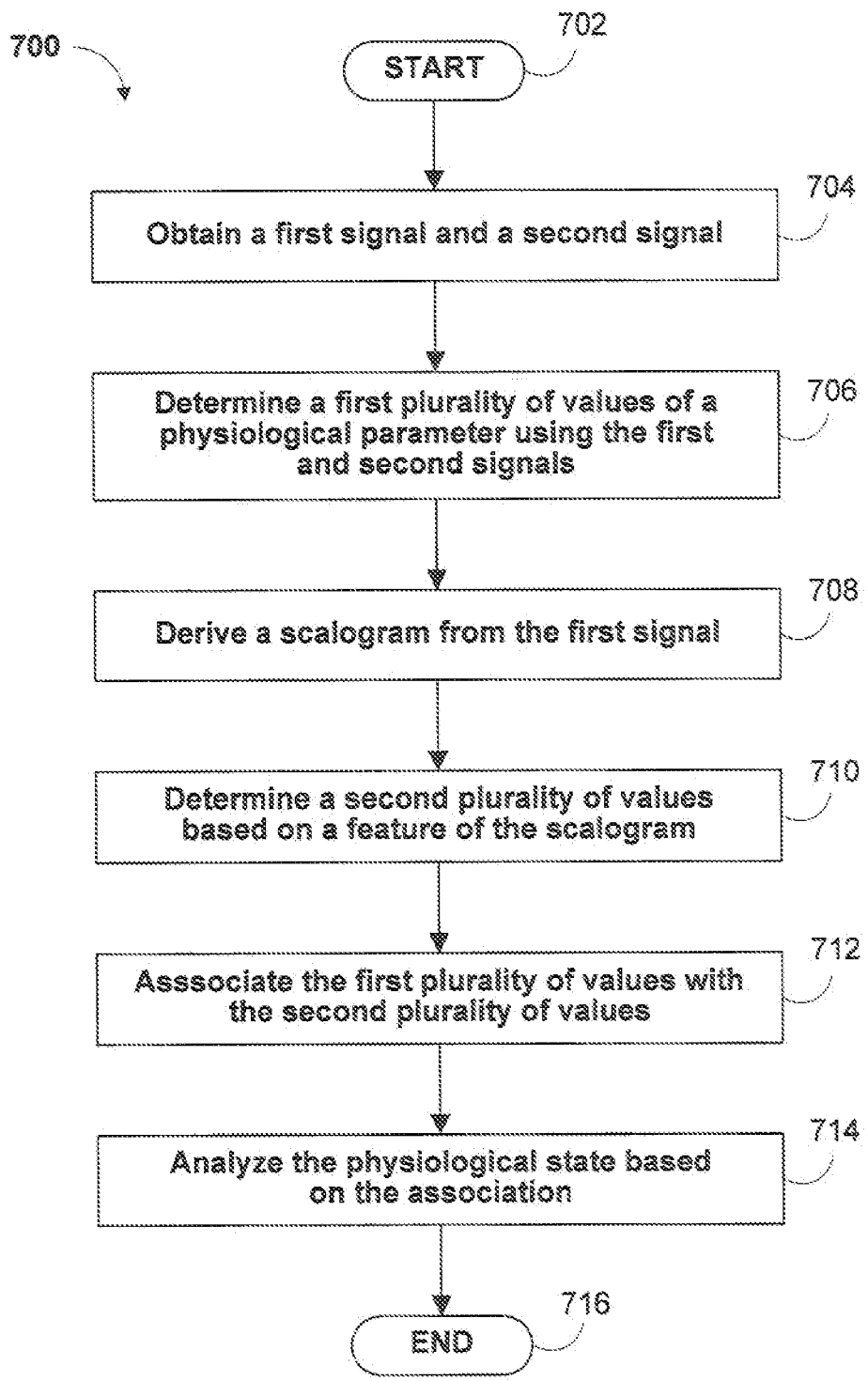
FIG. 7 is a flowchart of an illustrative process for analyzing a physiological state in accordance with an embodiment.

FIG. 7 is a flowchart of an illustrative process for analyzing a physiological state in accordance with an embodiment. Process 700 may begin at step 702. In embodiments, at step 704, a first signal and a second signal may be obtained in any suitable manner. For example, two PPG signals (e.g., red light signal 520 and infrared light signal 540) may be obtained from sensor 12 that may be coupled to patient 40 (FIG. 2). Alternatively, the PPG signals may be obtained from input signal generator 410, which may include oximeter 420 coupled to sensor 418, which may provide as input signal 416 (FIG. 4) PPG signals. In an embodiment, the PPG signals may be obtained from patient 40 using sensor 12 or input signal generator 410 in real time. In an embodiment, the PPG signals may have been stored in ROM 52, RAM 52, and/or QSM 72 (FIG. 2) in the past and may be accessed by microprocessor 48 within monitor 14 to be processed. In an embodiment, the first PPG signal may include a red light signal (e.g., signal 520) and the second PPG signal may include an infrared light signal (e.g., signal 540). The first and second PPG signals may be obtained simultaneously from patient 40.

In embodiments, at step 706, a first plurality of values related to a physiological parameter may be obtained in any suitable manner using at least the first signal and the second signal. For example, the first plurality of values may include blood oxygen saturation values derived by processor 412 or microprocessor 48 from red light signal 520 and infrared light signal 540 using any suitable approach as described above. The signals may be analyzed using the "ratio of ratios" method, or alternatively, a wavelet transform may be performed on one or more signals to generate one or more scalograms, as described above with respect to FIGS. 3(a) and 3(b) that may be further analyzed (e.g. to derive slope values and/or to create histograms) to obtain the blood oxygen saturation values. Processor 412 or microprocessor 48 may include any suitable software, firmware, and/or hardware, and/or combinations thereof for performing the calculations associated with the continuous wavelet transforms as well as the calculations associated with any suitable interrogations of the scalograms.

In embodiments, at step 708, a scalogram may be derived at least in part from the first signal. For example, a scalogram may be derived at least in part from infrared light signal 540 as described above with respect to FIGS. 3(a), 3(b), and 3(c) after infrared light signal 540 has been sent to microprocessor 48 or alternatively, to processor 412 (FIG. 4). In an embodiment, processor 412 or microprocessor 48 may perform the calculations associated with the continuous wavelet transforms of the signal.

In embodiments, at step 710, a second plurality of values may be determined using at least a feature of the scalogram in any suitable manner. For example, the second plurality of values may include respiration values derived by processor 412 or microprocessor 48 from a scalogram derived at least in part from infrared light signal 540. The respiration values may be derived by following a feature of the scalogram (e.g. the respiration band B, FIG. 3(c)) in wavelet space to obtain respiration scale values over a given period of time. Alternatively, the ridge of the pulse band of the scalogram (e.g. band A, FIG. 3(c)) may be followed in wavelet space and the RAP and RSP signals may be extracted as described above with respect to FIG. 3(d). Using SWFD, as described above, a further wavelet decomposition may be performed on the RAP and RSP signals to determine the respiration values.

In embodiments, at step 712, the first plurality of values may be associated with the second plurality of values using any suitable approach. For example, the blood oxygen saturation amplitude values obtained in step 708 may be plotted by processor 412 or microprocessor 48 as a function of each respiration scale value obtained in step 710. In an embodiment, the plot may be a parameter scatter plot. The plot may include any suitable shape, slope, or orientation. In an embodiment, the respiration rate may be computed by processor 412 or microprocessor 48 based at least in part on the ridge of the respiration band from the scalogram and the respiration rate may be plotted in place of the scale values of the ridge.

In embodiments, at step 714, the physiological state that may be based at least in part on the association at step 712 may be analyzed by system 10, system 400, or a user of system 10 or system 400 in any suitable manner. For example, the plot or the parameter scatter plot obtained from step 712 may be included within a threshold region where a plot of respiration scale values versus blood oxygen saturation values may be expected for any suitable number of healthy patients (e.g., a threshold region empirically derived using physiological data from a number of individuals), or may be expected for healthy patient 40 in particular (e.g., a threshold region initially calibrated using physiological data obtained only from patient 40). The plot or parameter scatter plot obtained in step 712, alternatively, may be included within a threshold region where a plot of respiration scale values versus blood oxygen saturation values are expected for any number of patients, or particularly patient 40, who have a health problem such as a ventilation perfusion mismatch. In an embodiment, the shape, or the distribution, of the data points plotted in step 712 may be used instead of or in addition to threshold regions to determine the ventilation of patient 40. For example, a slope (e.g., a dominant slope) of the data point distribution may be used. The slope of the data points can be determined by processor 412 or microprocessor 48 using any suitable method. If the slope derived at least in part from the plotted data distribution has a value above a certain threshold (e.g., the threshold may be stored in processor 412), for example, that may be an indication of proper ventilation of patient 40. If the derived slope has a value that falls below the threshold, that may be an indication of poor ventilation of patient 40. In embodiments, process 700 may then advance to step 716 and end.

The foregoing is merely illustrative of the principles of this disclosure and various modifications can be made by those skilled in the art without departing from the scope and spirit of the disclosure.

What is claimed is:

1. A method for analyzing a physiological state, comprising:
 obtaining a first signal and a second signal;
 determining a first plurality of values of a physiological parameter using at least the first signal and the second signal;
 deriving a scalogram from the first signal;
 determining a second plurality of values based at least in part on a feature in the scalogram;
 associating the first plurality of values with the second plurality of values; and
 analyzing the physiological state based at least in part on the associated first and second plurality of values.

2. The method of claim 1, wherein the first signal and the second signal are photoplethysmograph signals from a user.

3. The method of claim 2, wherein the analyzing the physiological state comprises analyzing a ventilation state of the user.

4. The method of claim 2, wherein the physiological parameter corresponds at least in part to blood oxygen saturation of the user.

5. The method of claim 1, wherein the determining a second plurality of values based at least in part on a feature in the scalogram comprises selecting a plurality of scale values based at least in part on a respiration ridge in the scalogram.

6. The method of claim 1, wherein the determining a second plurality of values based at least in part on a feature in the scalogram comprises deriving a plurality of respiration rate values based at least in part on a respiration ridge in the scalogram.

7. The method of claim 1, wherein the associating the first plurality of values with the second plurality of values comprises deriving a parameter scatter plot.

8. The method of claim 7, wherein the analyzing the physiological state further comprises analyzing whether the parameter scatter plot is located within a threshold region.

9. The method of claim 8, wherein the threshold region is calibrated based at least in part upon at least a first portion of the first signal and at least a first portion of the second signal.

10. The method of claim 8, wherein the analyzing the physiological state further comprises calculating a slope value from the parameter scatter plot.

11. The method of claim 10, wherein the slope value having a lower value than a threshold value indicates a generally poor physiological state.

\* \* \* \* \*